US011407952B2

(12) United States Patent
Leal et al.

(10) Patent No.: US 11,407,952 B2
(45) Date of Patent: Aug. 9, 2022

(54) METHOD OF PRODUCING A FUEL ADDITIVE

(71) Applicants: SABIC Global Technologies B.V., Bergen op Zoom (NL); Saudi Arabian Oil Company, Dhahran (SA)

(72) Inventors: Guillermo Leal, Riyadh (SA); Mohammed Bismillah Ansari, Riyadh (SA); Kareemuddin Mahaboob Shaik, Dhahran (SA); Hiren Shethna, Dhahran (SA); Zhonglin Zhang, Dhahran (SA)

(73) Assignees: SAUDI ARABIAN OIL COMPANY, Dhahran (SA); SABIC GLOBAL TECHNOLOGIES B.V., Bergen op Zoom (NL)

( * ) Notice: Subject to any disclaimer, the term of this patent is extended or adjusted under 35 U.S.C. 154(b) by 0 days.

(21) Appl. No.: 17/045,669

(22) PCT Filed: Apr. 18, 2019

(86) PCT No.: PCT/US2019/028092
§ 371 (c)(1),
(2) Date: Oct. 6, 2020

(87) PCT Pub. No.: WO2019/217049
PCT Pub. Date: Nov. 14, 2019

(65) Prior Publication Data
US 2021/0155862 A1 May 27, 2021

Related U.S. Application Data

(60) Provisional application No. 62/667,681, filed on May 7, 2018.

(51) Int. Cl.
*C10L 1/185* (2006.01)
*C07C 5/05* (2006.01)
(Continued)

(52) U.S. Cl.
CPC .............. *C10L 1/1852* (2013.01); *C07C 5/05* (2013.01); *C07C 29/04* (2013.01); *C10G 65/12* (2013.01);
(Continued)

(58) Field of Classification Search
CPC ........... C07C 29/04; C07C 41/06; C07C 5/05; C07C 31/12; C07C 11/08; C07C 43/046;
(Continued)

(56) References Cited

U.S. PATENT DOCUMENTS 3,061,654 A 10/1962 Gensheimer et al.
3,797,690 A 3/1974 Taylor et al.
(Continued)

FOREIGN PATENT DOCUMENTS

CN 1044804 C 8/1999
CN 1506344 A 6/2004
(Continued)

OTHER PUBLICATIONS

Bender et al.; "Selective Hydrogenation in Steam Cracking"; 21st Annual Saudi-Japan Symposium; Catalysts in Petroleum Refining & Petrochemicals; King Fahd University of Petroleum & Minerals; 2011; Abstract only; pp. 1-3.
(Continued)

*Primary Examiner* — Latosha Hines
(74) *Attorney, Agent, or Firm* — Cantor Colburn LLP

(57) ABSTRACT

A method of producing a fuel additive includes: passing a first process stream comprising C4 hydrocarbons through a methyl tertiary butyl ether synthesis unit producing a first recycle stream; passing the first recycle stream through a hydration unit producing the fuel additive and a second recycle stream; passing the second recycle stream through a
(Continued)

recycle hydrogenation unit and a deisobutanizer unit; and recycling the second recycle stream to the methyl tertiary butyl ether synthesis unit.

20 Claims, 1 Drawing Sheet

(51) Int. Cl.
| | | |
|---|---|---|
| C07C 29/04 | (2006.01) | |
| C10G 65/12 | (2006.01) | |
| C10G 69/04 | (2006.01) | |
| C10L 1/182 | (2006.01) | |
| C10L 10/10 | (2006.01) | |

(52) U.S. Cl.
CPC ............ *C10G 69/04* (2013.01); *C10L 1/1824* (2013.01); *C10L 10/10* (2013.01); *C10G 2300/4081* (2013.01)

(58) Field of Classification Search
CPC ............ C07C 2521/04; C07C 2523/42; C07C 2523/44; C07C 2523/46; C07C 2523/72; C07C 2523/75; C07C 2523/755; C10L 1/14; C10L 1/1824; C10L 1/1616; C10L 1/185; C10L 1/1852; C10L 10/10; C10G 11/18; C10G 45/00; C10G 45/32; C10G 47/00; C10G 65/12; C10G 69/04; C10G 69/06; C10G 2300/4081
See application file for complete search history.

(56) References Cited

U.S. PATENT DOCUMENTS

| | | | |
|---|---|---|---|
| 3,849,082 A | | 11/1974 | Kozlowski et al. |
| 3,912,463 A | | 10/1975 | Kozlowski et al. |
| 4,324,936 A | * | 4/1982 | Mikulicz ............... C07C 5/2767 585/329 |
| 4,334,890 A | | 6/1982 | Kochar et al. |
| 4,336,046 A | | 6/1982 | Schorre et al. |
| 4,356,339 A | | 10/1982 | Imaizumi et al. |
| 4,408,085 A | | 10/1983 | Gottlieb et al. |
| 4,423,251 A | * | 12/1983 | Pujado .................... C07C 11/09 585/737 |
| 4,455,445 A | | 6/1984 | Neuzil et al. |
| 4,499,313 A | | 2/1985 | Okumura et al. |
| 4,540,831 A | | 9/1985 | Briggs |
| 4,773,968 A | | 9/1988 | O'Connell et al. |
| 4,783,555 A | | 11/1988 | Atkins |
| 4,797,133 A | * | 1/1989 | Pujado ................ C07C 7/14891 44/449 |
| 4,927,977 A | | 5/1990 | Child et al. |
| 5,227,553 A | | 7/1993 | Polanek et al. |
| 5,254,748 A | | 10/1993 | Hensley et al. |
| 5,382,707 A | | 1/1995 | Rubin et al. |
| 5,523,502 A | | 6/1996 | Rubin |
| 5,563,299 A | | 10/1996 | Paludetto et al. |
| 5,628,880 A | | 5/1997 | Hearn et al. |
| 5,898,091 A | | 4/1999 | Chodorge et al. |
| 5,955,640 A | | 9/1999 | Paludetto et al. |
| 7,227,047 B2 | | 6/2007 | Risch et al. |
| 7,473,812 B2 | | 1/2009 | Peters et al. |
| 7,485,761 B2 | | 2/2009 | Schindler et al. |
| 8,124,572 B2 | | 2/2012 | Miller |
| 8,395,007 B2 | | 3/2013 | Wright et al. |
| 8,999,013 B2 | | 4/2015 | Xu et al. |
| 9,187,388 B2 | | 11/2015 | Arjah et al. |
| 9,611,192 B2 | | 4/2017 | Digiulio |
| 10,774,020 B2 | | 9/2020 | Di Girolamo et al. |
| 2002/0169346 A1 | | 11/2002 | Commereuc et al. |
| 2003/0158429 A1 | | 8/2003 | Albiez et al. |
| 2007/0265483 A1 | | 11/2007 | Himelfarb |
| 2009/0193710 A1 | | 8/2009 | Xiong et al. |
| 2011/0040133 A1 | | 2/2011 | Vermeiren et al. |
| 2011/0230632 A1 | | 9/2011 | Abhari |
| 2012/0117862 A1 | | 5/2012 | Xu |
| 2013/0072732 A1 | | 3/2013 | Breuil et al. |
| 2013/0104449 A1 | | 5/2013 | Xu et al. |
| 2013/0331620 A1 | | 12/2013 | Abhari |
| 2014/0039226 A1 | * | 2/2014 | Xu ..................... C10L 1/1824 568/899 |
| 2014/0142350 A1 | | 5/2014 | Weiner et al. |
| 2015/0225320 A1 | | 8/2015 | Shaik et al. |
| 2015/0322181 A1 | | 11/2015 | Kim et al. |
| 2016/0326079 A1 | | 11/2016 | Lee et al. |
| 2017/0198231 A1 | | 7/2017 | Xu et al. |
| 2020/0157450 A1 | | 5/2020 | Leal et al. |
| 2021/0002185 A1 | | 1/2021 | Leal et al. |
| 2021/0024837 A1 | | 1/2021 | Leal et al. |
| 2021/0024843 A1 | | 1/2021 | Leal et al. |
| 2021/0171848 A1 | | 6/2021 | Leal et al. |
| 2021/0214290 A1 | | 7/2021 | Ansari et al. |
| 2021/0246088 A1 | | 8/2021 | Leal et al. |

FOREIGN PATENT DOCUMENTS

| | | |
|---|---|---|
| CN | 101279879 A | 10/2008 |
| CN | 102070391 A | 5/2011 |
| CN | 105585411 A | 5/2016 |
| CN | 106608791 A | 5/2017 |
| CN | 102372573 A | 3/2021 |
| EP | 0063813 B1 | 11/1982 |
| EP | 0102840 B1 | 3/1984 |
| EP | 0253679 | 1/1988 |
| EP | 0605822 A1 | 7/1994 |
| GB | 1374368 | 11/1974 |
| JP | S5920232 A | 2/1984 |
| RU | 2470905 C1 | 12/2012 |
| WO | 9011268 | 10/1990 |
| WO | 9732838 A1 | 9/1997 |
| WO | 0043336 A1 | 7/2000 |
| WO | 0146095 A1 | 6/2001 |
| WO | 2006113191 A2 | 10/2006 |
| WO | 2007024733 A2 | 3/2007 |
| WO | 2012095744 A2 | 7/2012 |
| WO | 2014160825 A1 | 10/2014 |
| WO | 2015089005 A1 | 6/2015 |
| WO | 2015123026 A1 | 8/2015 |
| WO | 2019207477 A1 | 10/2019 |

OTHER PUBLICATIONS

Brockwell et al.; "Synthesize ethers"; Hydrocarbon Processing, vol. 70, No. 9; 1991; pp. 133-141.
International Search Report for International Application No. PCT/IB2019/052177; International Filing Date Mar. 18, 2019; dated Jun. 26, 2019; 3 pages.
International Search Report for International Application No. PCT/IB2019/052178; International Filing Date Mar. 18, 2019; dated Jun. 26, 2019; 6 pages.
International Search Report for International Application No. PCT/IB2019/053697; International Filing Date May 6, 2019; dated Aug. 28, 2019; 11 pages.
International Search Report for International Application No. PCT/IB2019/057784; International Filing Date Sep. 16, 2019; Date of Mailing Jan. 7, 2020; 5 pages.
International Search Report for International Application No. PCT/US2019/026985; International Filing Date Apr. 11, 2019; dated May 27, 2019; 6 pages.
International Search Report for International Application No. PCT/US2019/028099; International Filing Date Apr. 18, 2019; dated Jun. 26, 2019; 6 pages.
International Search Report; International Application No. PCT/IB2018/055647; International Filing Date: Jul. 27, 2018; dated Oct. 30, 2018; 6 pages.
Izquierdo et al.; "Equilibrium Constants for Methyl tert-Butyl Ether Liquid-Phas Synthesis"; J. Chem. Eng. Data, vol. 37; 1992; pp. 339-343.

(56) References Cited

OTHER PUBLICATIONS

Kalamaras et al.; "SuperButol—A novel high-octane gasoline blending component"; Fuel, vol. 195; 2017; pp. 165-173.
Streich et al.; "Secure the Best Benefits from C4 Hydrocarbon Processing—Part 1: Separation Sequences"; Hydrocarbon Processing: Process Engineering and Optimization; 2016; 6 pages.
Written Opinion for International Application No. PCT/IB2019/052177; International Filing Date Mar. 18, 2019; dated Jun. 26, 2019; 9 pages.
Written Opinion for International Application No. PCT/IB2019/052178; International Filing Date Mar. 18, 2019; dated Jun. 26, 2019; 9 pages.
Written Opinion for International Application No. PCT/IB2019/053697; International Filing Date May 6, 2019; dated Aug. 28, 2019; 9 pages.
Written Opinion for International Application No. PCT/IB2019/057784; International Filing Date Sep. 16, 2019; dated Jan. 7, 2020; 7 pages.
Written Opinion for International Application No. PCT/US2019/026985; International Filing Date Apr. 11, 2019; dated May 27, 2019; 7 pages.
Written Opinion for International Application No. PCT/US2019/028099; International Filing Date Apr. 18, 2019; dated Jun. 26, 2019; 13 pages.
Written Opinion; International Application No. PCT/IB2018/055647; International Filing Date: Jul. 27, 2018; dated Oct. 30, 2018; 11 pages.
Bodas et al.; U.S. Appl. No. 17/292,261; entitled "Process and System for Producing Ethylene and At Least One of Butanol and an Alkyl Tert-Butyl Ether"; filed with USPTO on May 7, 2021.
International Search Report for International Application No. PCT/IB2020/051908; International Filing Date Mar. 5, 2020; dated May 29, 2020; 6 pages.
Leal et al. U.S. Appl. No. 17/436,753, entitled "Method of Producing a Fuel Additive", filed with the USPTO on Sep. 7, 2021.
Written Opinion for International Application No. PCT/IB2020/051908; International Filing Date Mar. 5, 2020; dated May 29, 2020; 9 pages.
International Search Report for International Application No. PCT/US2019/028092; International Filing Date Apr. 18, 2019; dated Jun. 26, 2019; 6 pages.
Written Opinion for International Application No. PCT/US2019/028092; International Filing Date Apr. 18, 2019; dated Jun. 26, 2019; 9 pages.
International Search Report for International Application No. PCT/IB2019/059984; International Filing Date Nov. 20, 2019; dated Feb. 21, 2020; 5 pages.
Written Opinion for International Application No. PCT/IB2019/059984; International Filing Date Nov. 20, 2019; dated Feb. 21, 2020; 8 pages.

* cited by examiner

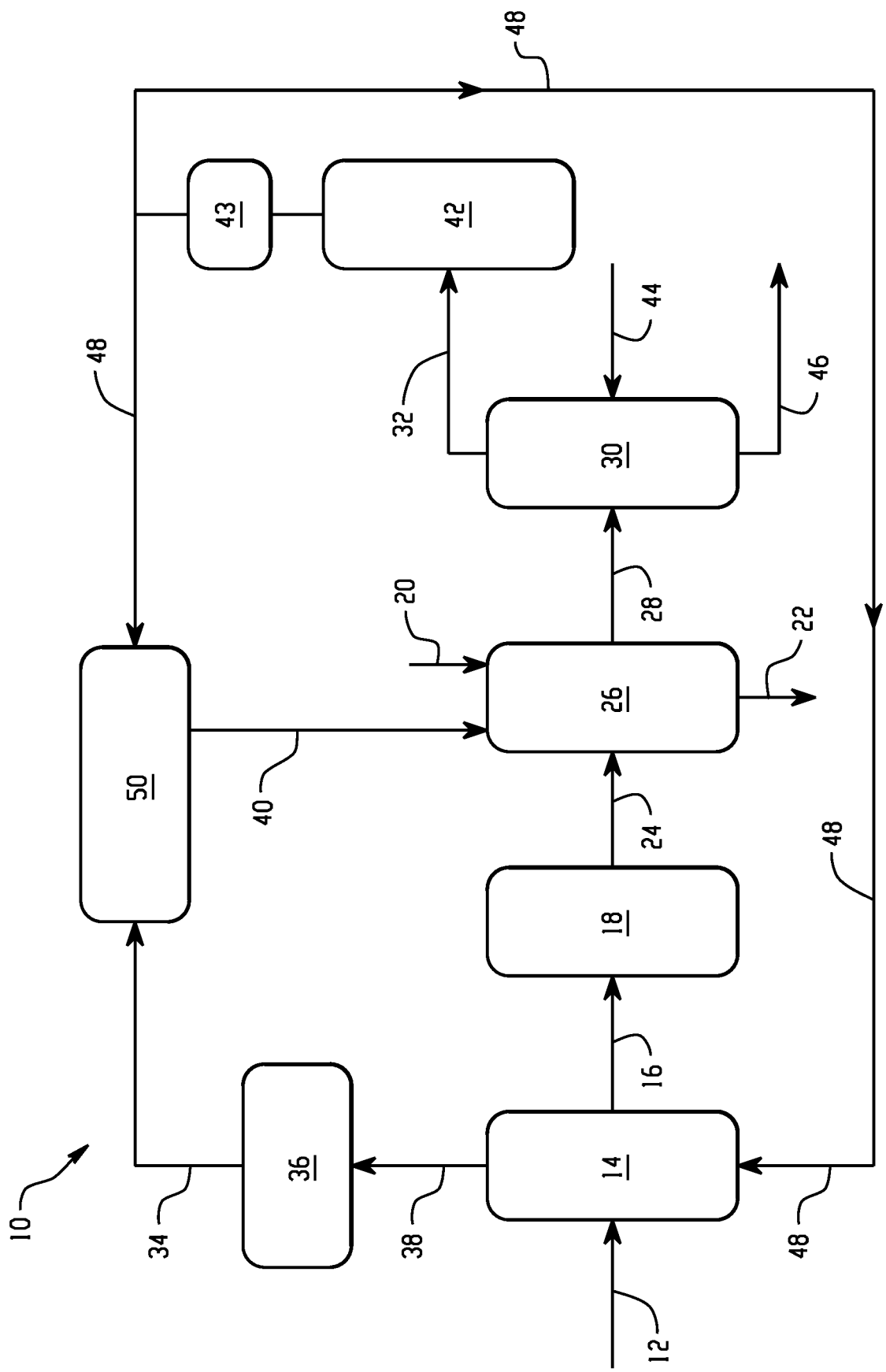

METHOD OF PRODUCING A FUEL ADDITIVE

CROSS REFERENCE TO RELATED APPLICATIONS

This application is a National Stage application of PCT/US2019/028092, filed Apr. 18, 2019, which is incorporated herein by reference in its entirety, and which claims the benefit of U.S. Provisional Application No. 62/667,681, filed May 7, 2018.

BACKGROUND

Commercial gasoline, which is fuel for internal combustion engines, is a refined petroleum product that is typically a mixture of hydrocarbons (base gasoline), additives, and blending agents. Additives and blending agents, for example octane boosters, are added to the base gasoline to enhance the performance and the stability of gasoline.

When used in high compression internal combustion engines, gasoline has the tendency to "knock." Knocking occurs when combustion of the air/fuel mixture in the cylinder does not start off correctly in response to ignition because one or more pockets of air/fuel mixture pre-ignite outside the envelope of the normal combustion front. Anti-knocking agents, also known as octane boosters, reduce the engine knocking phenomenon, and increase the octane rating of the gasoline.

Hydrocarbon cracking processes are important conversion processes used in petroleum refineries. For example, fluid catalytic cracking (FCC) is widely used to convert the high-boiling, high-molecular weight hydrocarbon fractions of petroleum crude oils to more valuable gasoline, olefinic gases, and other products. Thermal cracking of naphtha and gas oil is also widely used in the petrochemical industry to produce a variety of olefins and aromatics. For example, hydrocarbon feed stocks can be mixed with steam and subjected to elevated temperatures (e.g., 700-900° C.) in a steam cracker furnace wherein the feed stock components are cracked into various fractions. The effluent of the steam cracker can contain a gaseous mixture of hydrocarbons, for example, saturated and unsaturated olefins and aromatics (C1-C35). The effluent can then be separated into individual olefins (for example, ethylene, propylene and C4's) and pyrolysis gasoline. Recycle streams of crude hydrocarbons are often formed as byproducts during these cracking processes.

The presence of isobutylene, butadiene, 1-butene, 2-butene, and other components within the crude hydrocarbon streams can allow for the formation of valuable alcohols and fuel additives. However, the conversion of crude hydrocarbon streams to fuel additive products can often be inefficient and costly. Furthermore, the final product specifications for such alcohols can be undesirable and can fail to meet market quality requirements, all of which correlate with poor product quality. For example, alcohol products can have high levels of impurities, high Reid vapor pressures, e.g., greater than 2.0 pounds per square inch (psi) (greater than 10 kilopascals, greater than 12 kilopascals, greater than 13 kilopascals, greater than 14 kilopascals), and low octane numbers (e.g., 82 Research Octane Number (RON)), all of which correlate with poor product quality. Any improvement in these specifications and/or the efficiency of the process can provide a more valuable fuel additive product.

Thus, there is a need for an efficient method of producing fuel additives that can make use of crude hydrocarbon streams and produce final products with lower impurities and higher performance specifications.

SUMMARY

Disclosed, in various embodiments, are methods of producing fuel additives.

A method of producing a fuel additive comprises: passing a first process stream comprising C4 hydrocarbons through a methyl tertiary butyl ether synthesis unit producing a first recycle stream; passing the first recycle stream through a hydration unit producing the fuel additive and a second recycle stream; passing the second recycle stream through a recycle hydrogenation unit and a deisobutanizer unit; and recycling the second recycle stream to the methyl tertiary butyl ether synthesis unit.

A method of producing a fuel additive comprises: passing a first feed stream comprising C4 hydrocarbons through a fluid catalytic cracking unit forming a second feed stream; passing the second feed stream through a hydrogenation unit forming a first process stream; passing the first process stream through a methyl tertiary butyl ether synthesis unit producing a first recycle stream, wherein methanol and isobutylene are present in the methyl tertiary butyl ether synthesis unit in a molar ratio of one mole of isobutylene to 0.1 mole to 2 moles of methanol; withdrawing a methyl tertiary butyl ether product from the methyl tertiary butyl ether synthesis unit; withdrawing the first recycle stream from the methyl tertiary butyl ether synthesis unit and passing the first recycle stream through a hydration unit producing the fuel additive and a second recycle stream, wherein a temperature within the hydration unit is 30° C. to 200° C., a pressure within the hydration unit is 500 kiloPascals to 10,000 kiloPascals, and wherein greater than or equal to 90% by weight of any butene present in the first recycle stream is converted to butanol within the hydration unit; withdrawing the fuel additive from the hydration unit, wherein the fuel additive comprises 2-butanol, tert-butyl alcohol, di-isobutene, or a combination thereof; passing the second recycle stream through a recycle hydrogenation unit; passing the second recycle stream through a deisobutanizer unit forming an isobutylene-containing recycle stream; and recycling the isobutylene-containing recycle stream to the methyl tertiary butyl ether synthesis unit.

These and other features and characteristics are more particularly described below.

BRIEF DESCRIPTION OF THE DRAWING

The following is a brief description of the drawing wherein like elements are numbered alike and which are presented for the purposes of illustrating the exemplary embodiments disclosed herein and not for the purposes of limiting the same.

The FIGURE is a schematic diagram representing a unit sequence for producing fuel additives.

DETAILED DESCRIPTION

Disclosed herein is an efficient method of producing fuel additives that can make use of crude hydrocarbon streams and produce final products with low impurities and high performance specifications. For example, the method disclosed herein can provide a unique sequence of unit operations that converts crude hydrocarbons into valuable fuel additives, for example, alcohol fuel additives. This unique sequence can significantly improve the efficiency of the process thereby reducing total capital costs. The final fuel additive products can have levels of C4 dimers such as, for example, trimethylpentane of 0.01 weight % to 50 weight %, based on the total weight of the fuel additive, high octane numbers (e.g., greater than or equal to 85 RON, or greater than or equal to 87 RON), and low Reid vapor pressures of greater than or equal to 55 Kilopascals. For example, the trimethylpentane can be present in an amount of 0.1 to 25 weight percent, for example, 1 to 20 weight %. Any one or all of these properties can correlate with high performance and high market value. The method disclosed herein can also produce secondary products along with the fuel additive product. For example, methyl tertiary butyl ether (MTBE) products can be produced along with the fuel additive, thus maximizing the efficiency and productivity of the process.

The method can include passing a first feed stream of crude hydrocarbons through a hydrocarbon cracking unit forming a second feed stream which is then passed through a selective hydrogenation unit forming a first process stream. This hydrogenation unit can convert the butadiene present in the second feed stream to 1-butene and 2-butene. The minimization of butadiene in the process increases desirable product specifications such as the octane number. The first process stream can then be passed through a MTBE unit producing a first recycle stream. The MTBE unit can convert isobutylene present in the first process stream to a MTBE product and a first recycle stream. The first recycle stream can then be passed through a hydration unit to produce a fuel additive, for example, an alcohol fuel additive. A second recycle stream can also be produced in the hydration unit. The second recycle stream can be sent through an additional hydrogenation unit (e.g., a recycle hydrogenation unit) and a deisobutanizer unit, which can also comprise an isomerization unit and a dehydrogenation unit and which can produce an isobutylene-containing stream (also referred to herein as a deisobutanized recycle stream that can then be returned to the MTBE unit). The present process can maximize product quality for a fuel additive product while also producing additional MTBE products in an efficient manner.

The method disclosed herein can include passing a first feed stream through an olefin production unit, for example, a hydrocarbon cracking unit, for example, a catalytic and/or steam cracking unit, to produce a second feed stream, such that the second feed stream can include a product of an olefin cracking process and/or an olefin production process. The first feed stream can comprise hydrocarbons, for example, C4 hydrocarbons. The second feed stream can be withdrawn from the olefin production unit as a crude C4 hydrocarbon stream. The second feed stream produced by the olefin production unit can comprise propane, propylene, ethyl acetylene, vinyl acetylene, 1,3-butadiene, 1,2-butadiene, isobutylene, cis-2-butene, trans-2-butene, 1-butene, isobutane, n-butane, or a combination thereof. The total C4 olefin content of the second feed stream when withdrawn from a steam cracking unit can be greater than or equal to 90% by weight and the feed stream can comprise greater than or equal to 40% by weight isobutylene. The total C4 olefin content of the second feed stream when withdrawn from a fluid catalytic cracking unit can be greater than or equal to 50% by weight and the second feed stream can comprise greater than or equal to 30% by weight isobutane.

The second feed stream can be passed through a hydrogenation unit, for example a selective hydrogenation unit. For example, the hydrogenation unit can be a selective butadiene hydrogenation unit. The hydrogenation unit can convert butadiene present in the second feed stream to 1-butene, cis-2-butene and trans-2-butene. The conversion rate from butadiene to 1-butene, cis-2-butene and trans-2-butene can be greater than or equal to 90% by weight. Propylene, ethyl acetylene, and vinyl acetylene present in the second feed stream can undergo hydrogenation within the hydrogenation unit. The hydrogenation unit can comprise multiple reactors in series, for example, the unit can comprise three reactor stages. The first two reactor stages can convert butadiene present in the first process stream to 2-butene, cis-2-butene and trans-2-butene. The first two reactor stages can comprise a selective hydrogenation catalyst. For example, the hydrogenation catalyst can comprise palladium with an aluminum base. The hydrogenation catalyst can comprise platinum, rhodium, palladium, ruthenium, cobalt, nickel, copper, or a combination thereof. The catalyst can be the same for the first two reactor stages. Hydrogen can be injected into the second feed stream prior to passing through the first reactor stage.

Final hydrogenation of di-olefins to a desired product of mono-olefin can be achieved in the third reactor. Carbon monoxide can be injected into the third reactor to attenuate the catalyst and minimize the isomerization reaction from 1-butene to 2-butene. During normal operations, the desired carbon monoxide injection rate can be 2 parts per million of the feed stream to the third reactor. The rate can be increased if too much 1-butene is being lost to 2-butene. The first process stream can then be withdrawn from the selective hydrogenation unit. Operation conditions for the selective hydrogenation unit are shown in Table 1. Temperature is reported in degrees Celsius and pressure in pounds per square inch gage and kiloPascals.

TABLE 1

| Reactor | Temp °C. | Pressure (psig) | Catalyst | Representative BD content at exit |
|---|---|---|---|---|
| 1st Reactor | 40-70 | 140-400 (965-2758 kPa) | Noble metal/Alumina | 7% |
| 2nd Reactor | 50-60 | 140-400 (965-2758 kPa) | Noble metal/Alumina | 1% |
| 3rd Reactor | 60-80 | 250-270 (1724-1862 kPa) | Noble metal/Alumina | <0.01% |

The first process stream exiting the hydrogenation unit can then be passed through a MTBE unit producing a first recycle stream. The first process stream entering the MTBE unit can comprise less than or equal to 5% by weight butadiene, for example, less than or equal to 3% by weight, for example, less than or equal to 1% by weight. Methanol can be fed through the MTBE unit via a methanol stream. The MTBE unit can convert isobutylene present in the first process stream to a MTBE product. The first process stream can be contacted with the methanol and a catalyst, for example, an acid-type ion-exchange resin catalyst, within the MTBE unit. Methanol and isobutylene can be present within the MTBE unit in a molar ratio of 1.0 mole of isobutylene to 0.1 moles to 5 moles of methanol, for example, one mole of isobutylene to 0.5 moles to 2.0 moles of methanol, for example, one mole of isobutylene to 1.06 moles to 1.2 moles of methanol. The MTBE product can be withdrawn from the MTBE unit via a MTBE product stream. The purity of the MTBE product can be greater than or equal to 95%. The conversion rate from isobutylene to MTBE within the MTBE unit can greater than or equal to 75%, for example, greater than or equal to 85%, for example, greater than or equal to 95%. The first process stream can then be withdrawn from the MTBE unit as a first recycle stream with reduced isobutylene content. For example, the first recycle stream exiting the MTBE unit can comprise less than or equal to 5% by weight isobutylene. A temperature within the MTBE unit can be 15° C. to 150° C., for example, 35° C. to 125° C. A pressure within the MTBE unit can be 500 kiloPascals to 2800 kiloPascals, for example, 1000 kiloPascals to 2000 kiloPascals, for example, 1500 kiloPascals.

The first recycle stream exiting the MTBE unit can then be passed through a hydration unit to produce a fuel additive product, for example, an alcohol fuel additive. The first recycle stream entering the hydration unit can comprise less than or equal to 5% butadiene by weight, for example, less than or equal to 3%, for example, less than or equal to 1%. The fuel additive product can be withdrawn from the hydration unit via a fuel additive product stream. Water can be fed to the hydration unit via a water stream. The hydration unit can comprise an oscillating baffle reactor, a fixed bed reactor, a membrane integrated reactor, or a combination thereof. The hydration unit can convert butene present in the first process stream to butanol. For example, greater than or equal to 90% by weight of the butene present in the first recycle stream can be converted to butanol within the hydration unit. The first recycle stream can be contacted with water and a catalyst within the hydration unit. For example, the catalyst can comprise phosphoric acid, hypophosphorous acid, an ion-exchange resin, sulfur, polystyrene, polymer, niobium oxide, or a combination thereof. Water and butene can be present within the hydration unit in a molar ratio of 1.0 mole of water to 1 mole to 20 moles of butene, for example, one mole of water to 5 moles to 10 moles of butene. A temperature within the hydration unit can be 30° C. to 250° C., for example, 100° C. to 200° C. A pressure within the hydration unit can be 500 kiloPascals to 20,000 kiloPascals, for example, 5000 kiloPascals to 10,000 kiloPascals, for example, 7500 kiloPascals.

The fuel additive product can comprise 2-butanol, tert-butyl alcohol, C4-dimer, or a combination thereof, for example, the C4-dimer can comprise di-isobutylene, 2,2,4 trimethylpentane, 2,3,3 trimethylpentane, or a combination thereof. There is no particular restriction on the relative amounts of each of the foregoing components in the C4-dimer composition. The fuel additive product can comprise greater than or equal to 0.1% by weight trimethylpentane, for example, greater than or equal to 0.5% by weight, for example, greater than or equal to 1.0% by weight. In some instances, the fuel additive product can comprise 10% by weight to 20% by weight trimethylpentane. An octane number of the fuel additive product can be greater than or equal to 80 according to the Anti-Knock Index, for example, greater than or equal to 83.

The octane number is a standard measurement used to gage the performance of an engine or fuel. The higher the octane number, the more compression the fuel is able to withstand before igniting. Fuels with higher octane ratings are generally used in high performance gasoline engines that need higher compression ratios. Fuels with lower octane numbers can be desirable for diesel engines because diesel engines do not compress the fuel, but rather compress only air and then inject fuel into the air which is heated by compression. Gasoline engines rely on ignition of air and fuel compressed together as a mixture, which is ignited at the end of the compression stroke using spark plugs. As a result, high compressibility of fuel is a consideration for gasoline engines.

The Anti-Knock Index is measured by adding the research octane number and the motor octane number and dividing by two, i.e., (RON+MON)/2. The Research Octane Number is determined by running the fuel in a test engine at a speed of 600 revolutions per minute with a variable compression ratio under controlled conditions, and comparing the results with those for mixtures of iso-octane and n-heptane. Motor Octane Number is determined by testing a similar test engine to that used in determining the Research Octane Number but at a speed of 900 revolutions per minute with a preheated fuel mixture, higher engine speed, and variable ignition timing. Depending on the composition, the Motor Octane Number can be about 8 to 12 octanes lower than the Research Octane Number. The research octane number can be greater than or equal to 80, for example, greater than or equal to 85, for example, greater than or equal to 91, for example, greater than or equal to 95. The motor octane number can be greater than or equal to 70, for example, greater than or equal to 75, for example, greater than or equal to 80, for example, greater than or equal to 82 for example, greater than or equal to 85, for example, greater than or equal to 90, for example, greater than or equal to 95.

It can be desirable for a fuel blending component such as the fuel additive disclosed herein to have a higher or equivalent RON/MON as compared to a base gasoline since the main purpose is to increase the gasoline volumes and octane number. Base (or straight run) gasoline generally has have a RON of around 70 and refineries blend reformates to a RON of approximately 105 and alkylates to a RON of approximately 96 to increase the base gasoline RON to a value higher than 85. Oxygenates can then be added to further increase the RON to 91, 95, and even higher. Thus, it can be seen that the addition of oxygenates to gasoline for fuel blending desirably have a RON of greater than 85. Generally, the octane sensitivity for alkylates and reformates can be very low, meaning that the difference between RON and MON can be low, for example, about 6 to about 7. This can desirable for refineries located in the United States.

Higher octane ratings can give higher amounts of energy needed to initiate combustion. Fuels with higher octane ratings are less prone to auto-ignition and can withstand a greater rise in temperature during the compression stroke of an internal combustion engine without auto-igniting.

Reid vapor pressure is used to measure the volatility of gasoline defined as the absolute vapor pressure exerted by a liquid at 37.8° C. as determined by ASTM D-323. The measures the vapor pressure of gasoline volatile crude oil, and other volatile petroleum products, except for liquefied petroleum gases. Reid vapor pressure is measured in kiloPascals and represents a relative pressure to atmospheric pressure since ASTM D-323 measures the gage pressure of the sample in a non-evacuated chamber. High levels of vaporization are desired for winter staring and operation and lower levels are desirable in avoiding vapor lock during summer heat. Fuel cannot be pumped when vapor is present in the fuel line and winter starting will be difficult when liquid gasoline in the combustion chambers has not vaporized. This means that the Reid vapor pressure is changed accordingly by oil producers seasonally to maintain gasoline engine reliability.

The Reid vapor pressure of the fuel additive product can be less than or equal to 55 kiloPascals, for example, 5 kiloPascals to 55 kiloPascals, for example, 8 kiloPascals to 53 kiloPascals. The Reid vapor pressure can vary during winter and summer conditions such that the pressure can be at the higher end of the values during the winter and at the lower end of the values during the summer. The fuel additive product can also comprise less than or equal to 1% by weight impurities such as diene. For example, the fuel additive product can comprise less than or equal to 0.1% by weight of butylene dimers.

A second recycle stream, for example, a hydrocarbon recycle stream, can be withdrawn from the hydration unit and passed through a recycle hydrogenation unit to form a hydrogenated recycle stream. Optionally, the second recycle stream can be passed through a drying unit, e.g., for trace water removal before or after passing through the recycle hydrogenation unit. The recycle stream can comprise 1-butene, 2-butene, isobutane, n-butane, or a combination thereof. The recycle hydrogenation unit can convert any olefin present in the second recycle stream to the corresponding paraffin. For example, greater than or equal to 90% of any butene present in the second recycle stream can be converted to butane within the recycle hydrogenation unit.

The resulting hydrogenated recycle stream can optionally be recycled to the hydrocracking unit. The hydrogenated recycle stream can also optionally be further passed through a deisobutanizer unit and then returned to the MTBE unit via an isobutylene-containing recycle stream. The deisobutanizer unit can comprise a deisobutanizer column, and isomerization unit, followed by a dehydrogenation unit in series. The deisobutanizer column can be operated at a temperature of 50 to 120° C. and a pressure of 800 to 100 kilopascals. The isomerization unit can be operated with a platinum based catalyst having a $H_2$ to HC ratio of 0.03, a liquid hourly space velocity of 4.0 $m^3/h/m^3$ of catalyst, at a temperature of 120 180° C., and a pressure of 2900 to 3500 kilopascals. The dehydrogenation unit can be operated at a temperature of 550 to 680° C., at a pressure of 20 to 120 kilopascals, with a catalyst comprising chromium alumina, platinum, tin, zinc oxide, or a combination thereof. The dehydrogenation unit can include an adiabatic moving-bed reactor, adiabatic fixed-bed reactor, isothermal fixed-bed reactor, fluidized bed reactor, or a combination thereof. The deisobutanizer unit can convert the butane present in the hydrogenated recycle stream to isobutylene. For example, greater than or equal to 40% of any butane present in the process stream can be converted to isobutylene prior to recycling the process stream back to the MTBE unit.

A secondary hydrocarbon stream can optionally be withdrawn from the hydrocarbon cracking unit and passed through a total hydrogenation unit to produce a total hydrogenated stream. The hydrocarbon cracking unit can be operated at a temperature of 25 to 80° C., at a pressure of 650 to 3000 kilopascals (e.g., 100 to 400 pounds per square inch), with a catalyst comprising palladium with an aluminum base, platinum, rhodium, palladium, ruthenium, cobalt, nickel, copper, or a combination thereof. The total hydrogenation unit can convert greater than or equal to 99% of the olefins present in the secondary hydrocarbon stream to alkanes. The total hydrogenated stream can then be fed to the deisobutanizer unit.

A more complete understanding of the components, processes, and apparatuses disclosed herein can be obtained by reference to the accompanying drawings. These FIGURES (also referred to herein as "FIG.") are merely schematic representations based on convenience and the ease of demonstrating the present disclosure, and are, therefore, not intended to indicate relative size and dimensions of the devices or components thereof and/or to define or limit the scope of the exemplary embodiments. Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function.

Referring now to the FIGURE, this simplified schematic diagram represents a unit sequence 10 used in a method for producing fuel additives. The sequence 10 can include passing a first feed stream 12 comprising hydrocarbons through a hydrocarbon cracking unit 14. For example, the hydrocarbon cracking unit 14 can be a steam cracking and/or a catalytic cracking unit.

A second feed stream 16 can then be withdrawn from the hydrocarbon cracking unit 14. The second feed stream 16 can comprise crude hydrocarbons, for example, C4 hydrocarbons. The second feed stream 16 can be passed through a hydrogenation unit 18. The hydrogenation unit 18 can be a selective butadiene hydrogenation unit and can comprise multiple reactors in series. This hydrogenation unit 18 can convert butadiene present in the second feed stream 16 to 2-butene.

A first process stream 24 can be withdrawn from the selective hydrogenation unit 18. The first process stream 24 can then be passed through a MTBE unit 26. Methanol can be fed through the MTBE unit 26 via stream 20. The MTBE unit 26 can convert isobutylene present in the first process stream 24 to an MTBE product 22. This MTBE product 22 can be withdrawn from the MTBE unit 24. A first recycle stream 28 can then be withdrawn from the MTBE unit 26, now comprising a reduced isobutylene content.

The first recycle stream 28 can then be passed through a hydration unit 30 to produce a fuel additive product 46, for example, an alcohol fuel additive. The fuel additive product 46 can be withdrawn from the hydration unit 30. Water can be fed to the hydration unit via stream 44.

A second recycle stream 32, for example, a hydrocarbon recycle stream, can be withdrawn from the hydration unit 30 and recycled back to the MTBE unit 26 after passing through a recycle hydrogenation unit 42 and a deisobutanizer unit 50. The second recycle stream 32 can optionally passed through a dryer 43 after the recycle hydrogenation unit 42. The resulting hydrogenated recycle stream 48 can be further passed through the deisobutanizer unit 50 before returning to the MTBE unit 26 via the deisobutanized recycle stream 40. The deisobutanizer unit 50 can comprise a deisobutanizer column, isomerization unit, and a dehydrogenation unit in series. The deisobutanizer unit 50 can convert the isobutane present in the hydrogenated recycle stream 48 to isobutylene. The resulting hydrogenated recycle stream 48 can optionally be recycled to the hydrocracking unit 14.

A secondary hydrocarbon stream 38 can optionally be withdrawn from the hydrocarbon cracking unit 14 and passed through a total hydrogenation unit 36 to produce a total hydrogenated stream 34. The total hydrogenation unit 36 can convert olefins present in the secondary hydrocarbon stream 38 to alkenes. The total hydrogenated stream 34 can then be fed to the deisobutanizer unit 50.

The methods disclosed herein include(s) at least the following aspects:

Aspect 1: A method of producing a fuel additive, comprising: passing a first process stream comprising C4 hydrocarbons through a methyl tertiary butyl ether synthesis unit producing a first recycle stream; passing the first recycle stream through a hydration unit producing the fuel additive and a second recycle stream; passing the second recycle stream through a recycle hydrogenation unit and a deisobutanizer unit; and recycling the second recycle stream to the methyl tertiary butyl ether synthesis unit.

Aspect 2: The method of Aspect 1, wherein a source of the first process stream comprises a product of an olefin cracking process and/or an olefin production process, wherein the first process stream comprises propane, propylene, ethyl acetylene, vinyl acetylene, 1,3-butadiene, 1,2-butadiene, isobutylene, cis-2-butene, trans-2-butene, 1-butene, isobutane, n-butane, or a combination thereof.

Aspect 3: The method of any of the preceding aspects, further comprising passing a first feed stream through a hydrocracking unit, forming a second feed stream and passing the second feed stream through a selective hydrogenation unit prior to passing through the methyl tertiary butyl ether synthesis unit, forming the first process stream.

Aspect 4: The method of any of the preceding aspects, further comprising contacting the first process stream with a catalyst within the methyl tertiary butyl ether synthesis unit, wherein the catalyst comprises an acid-type ion-exchange resin.

Aspect 6: The method of any of the preceding aspects, wherein a temperature within the methyl tertiary butyl ether synthesis unit is 15° C. to 150° C. and a pressure within the methyl tertiary butyl ether unit is 500 kiloPascals to 2800 kiloPascals.

Aspect 6: The method of any of the preceding aspects, wherein methanol and isobutylene are present in the methyl tertiary butyl ether unit in a molar ratio of one mole of isobutylene to 0.1 mole to 5 moles of methanol; preferably, one mole of isobutylene to 1.06 moles to 1.2 moles of methanol.

Aspect 7: The method of any of the preceding aspects, wherein greater than or equal to 90% by weight of any isobutylene present in the first process stream is converted to methyl tertiary butyl ether within the methyl tertiary butyl ether unit, and further comprising withdrawing the methyl tertiary butyl ether as a product from the methyl tertiary butyl ether synthesis unit.

Aspect 8: The method of any of Aspects 3-7, wherein the first recycle stream comprises less than or equal to 3.0% by weight butadiene prior to passing through the hydration unit.

Aspect 9: The method of any of Aspects 3-8, wherein a temperature within the hydration unit is 30° C. to 250° C. and a pressure within the hydration unit is 500 kiloPascals to 20,000 kiloPascals.

Aspect 10: The method of any of the preceding aspects, wherein greater than or equal to 90% by weight of any butene present in the first recycle stream is converted to butanol within the hydration unit.

Aspect 11: The method of any of the preceding aspects, further comprising withdrawing a fuel additive product from the hydration unit.

Aspect 12: The method of Aspect 11, wherein the fuel additive product comprises 2-butanol, tert-butyl alcohol, a C4-dimer, or a combination thereof, preferably, wherein the C4-dimer comprises di-isobutylene, 2,2,4 trimethylpentane, 2,3,3 trimethylpentane, or a combination thereof.

Aspect 13: The method of Aspect 12, wherein an octane number of the fuel additive product is greater than or equal to 80 in accordance with the Anti-Knock Index, preferably wherein the octane number is greater than or equal to 83.

Aspect 14: The method of Aspect 12, wherein a Reid vapor pressure of the fuel additive product is less than or equal to 55 kiloPascals; preferably, wherein the Reid vapor pressure is 8 kiloPascals to 53 kiloPascals.

Aspect 15: The method of any of the preceding aspects, wherein greater than or equal to 90% by weight of any butene present in the second recycle stream is converted to butane within the recycle hydrogenation unit.

Aspect 16: The method of any of the preceding aspects, further comprising drying the second recycle stream before or after passing to the recycle hydrogenation unit.

Aspect 17: The method of any of the preceding aspects, wherein greater than or equal to 40% by weight of any butane present in the second recycle stream is converted to isobutylene in the deisobutanizer unit prior to recycling to the methyl tertiary butyl ether synthesis unit.

Aspect 18: A method of producing a fuel additive, comprising: passing a first feed stream comprising C4 hydrocarbons through a fluid catalytic cracking unit forming a second feed stream; passing the second feed stream through a hydrogenation unit forming a first process stream; passing the first process stream through a methyl tertiary butyl ether synthesis unit producing a first recycle stream, wherein methanol and isobutylene are present in the methyl tertiary butyl ether synthesis unit in a molar ratio of one mole of isobutylene to 0.1 mole to 2 moles of methanol; withdrawing a methyl tertiary butyl ether product from the methyl tertiary butyl ether synthesis unit; withdrawing the first recycle stream from the methyl tertiary butyl ether synthesis unit and passing the first recycle stream through a hydration unit producing the fuel additive and a second recycle stream, wherein a temperature within the hydration unit is 30° C. to 200° C., a pressure within the hydration unit is 500 kiloPascals to 10,000 kiloPascals, and wherein greater than or equal to 90% by weight of any butene present in the first recycle stream is converted to butanol within the hydration unit; withdrawing the fuel additive from the hydration unit, wherein the fuel additive comprises 2-butanol, tert-butyl alcohol, di-isobutene, or a combination thereof; passing the second recycle stream through a recycle hydrogenation unit; passing the second recycle stream through a deisobutanizer unit forming an isobutylene-containing recycle stream; and recycling the isobutylene-containing recycle stream to the methyl tertiary butyl ether synthesis unit.

Aspect 19: The method of Aspect 18, wherein the deisobutanizer unit comprises a deisobutanizer column, an isomerization unit, and a dehydrogenation unit.

In general, the invention may alternately comprise, consist of, or consist essentially of, any appropriate components herein disclosed. The invention may additionally, or alternatively, be formulated so as to be devoid, or substantially free, of any components, materials, ingredients, adjuvants or species used in the prior art compositions or that are otherwise not necessary to the achievement of the function and/or objectives of the present invention. The endpoints of all ranges directed to the same component or property are inclusive and independently combinable (e.g., ranges of "less than or equal to 25 wt %, or 5 wt % to 20 wt %," is inclusive of the endpoints and all intermediate values of the ranges of "5 wt % to 25 wt %," etc.). Disclosure of a narrower range or more specific group in addition to a broader range is not a disclaimer of the broader range or larger group. Furthermore, the terms "first," "second," and the like, herein do not denote any order, quantity, or importance, but rather are used to denote one element from another. The terms "a" and "an" and "the" herein do not denote a limitation of quantity, and are to be construed to cover both the singular and the plural, unless otherwise indicated herein or clearly contradicted by context. "Or" means "and/or." The suffix "(s)" as used herein is intended to include both the singular and the plural of the term that it modifies, thereby including one or more of that term (e.g., the film(s) includes one or more films). Reference throughout the specification to "one embodiment", "another embodiment", "an embodiment", and so forth, means that a particular element (e.g., feature, structure, and/or characteristic) described in connection with the embodiment is included in at least one embodiment described herein, and may or may not be present in other embodiments. In addition, it is to be understood that the described elements may be combined in any suitable manner in the various embodiments.

The modifier "about" used in connection with a quantity is inclusive of the stated value and has the meaning dictated by the context (e.g., includes the degree of error associated with measurement of the particular quantity). The notation "±10%" means that the indicated measurement can be from an amount that is minus 10% to an amount that is plus 10% of the stated value. The terms "front", "back", "bottom", and/or "top" are used herein, unless otherwise noted, merely for convenience of description, and are not limited to any one position or spatial orientation. "Optional" or "optionally" means that the subsequently described event or circumstance can or cannot occur, and that the description includes instances where the event occurs and instances where it does not. Unless defined otherwise, technical and scientific terms used herein have the same meaning as is commonly understood by one of skill in the art to which this invention belongs. A "combination" is inclusive of blends, mixtures, alloys, reaction products, and the like. In a list of alternatively useable species, "a combination thereof" means that the combination can include a combination of at least one element of the list with one or more like elements not named. Also, "at least one of" means that the list is inclusive of each element individually, as well as combinations of two or more elements of the list, and combinations of at least one element of the list with like elements not named.

All cited patents, patent applications, and other references are incorporated herein by reference in their entirety. However, if a term in the present application contradicts or conflicts with a term in the incorporated reference, the term from the present application takes precedence over the conflicting term from the incorporated reference While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications variations, improvements, and substantial equivalents.

What is claimed is:

1. A method of producing a fuel additive, comprising:
   passing a first process stream comprising C4 hydrocarbons through a methyl tertiary butyl ether synthesis unit producing a first recycle stream and a methyl tertiary butyl ether product;
   passing the first recycle stream through a hydration unit producing the fuel additive and a second recycle stream;
   passing the second recycle stream through a recycle hydrogenation unit, wherein at least a portion of butene present in the second recycle stream is converted to butane within the recycle hydrogenation unit;
   passing the second recycle stream from the recycle hydrogenation unit and through a deisobutanizer unit; and
   recycling the second recycle stream from the deisobutanizer unit to the methyl tertiary butyl ether synthesis unit;
   wherein greater than or equal to 40% by weight of any butane present in the second recycle stream is converted to isobutylene in the deisobutanizer unit prior to recycling to the methyl tertiary butyl ether synthesis unit.

2. The method of claim 1, wherein a source of the first process stream comprises a product of an olefin cracking process and/or an olefin production process, wherein the first process stream comprises at least one of propane, propylene, ethyl acetylene, vinyl acetylene, 1,3-butadiene, 1,2-butadiene, isobutylene, cis-2-butene, trans-2-butene, 1-butene, isobutane, or n-butane.

3. The method of claim 1, further comprising passing a first feed stream through a hydrocracking unit, forming a second feed stream and passing the second feed stream through a selective hydrogenation unit prior to passing through the methyl tertiary butyl ether synthesis unit, forming the first process stream.

4. The method of claim 1, further comprising contacting the first process stream with a catalyst within the methyl tertiary butyl ether synthesis unit, wherein the catalyst comprises an acid-type ion-exchange resin;
   wherein the first recycle stream exiting the methyl tertiary butyl ether synthesis unit comprises less than or equal to 5% isobutylene by weight; and
   wherein the purity of the methyl tertiary butyl ether product is greater than or equal to 95%.

5. The method of claim 1, wherein a temperature within the methyl tertiary butyl ether synthesis unit is 15° C. to 150° C. and a pressure within the methyl tertiary butyl ether synthesis unit is 500 kiloPascals to 2800 kiloPascals.

6. The method of claim 1, wherein methanol and isobutylene are present in the methyl tertiary butyl ether synthesis unit in a molar ratio of one mole of isobutylene to 0.1 mole to 5 moles of methanol.

7. The method of claim 1, wherein greater than or equal to 90% by weight of any isobutylene present in the first process stream is converted to methyl tertiary butyl ether within the methyl tertiary butyl ether synthesis unit, and further comprising withdrawing the methyl tertiary butyl ether product from the methyl tertiary butyl ether synthesis unit.

8. The method of claim 1, wherein the first recycle stream comprises less than or equal to 3.0% by weight butadiene prior to passing through the hydration unit.

9. The method of claim 1, wherein a temperature within the hydration unit is 30° C. to 250° C. and a pressure within the hydration unit is 500 kiloPascals to 20,000 kiloPascals.

10. The method of claim 1, wherein greater than or equal to 90% by weight of any butene present in the first recycle stream is converted to butanol within the hydration unit.

11. The method of claim 1, further comprising withdrawing a fuel additive product from the hydration unit.

12. The method of claim 11, wherein the fuel additive product comprises at least one of 2-butanol, tert-butyl alcohol, or a C4-dimer, and wherein the fuel additive product comprises 1 to 25 weight % of trimethylpentane.

13. The method of claim 12, wherein an octane number of the fuel additive product is greater than or equal to 80 in accordance with the Anti-Knock Index.

14. The method of claim 12, wherein a Reid vapor pressure of the fuel additive product is less than or equal to 55 kiloPascals.

15. The method of claim 1, wherein greater than or equal to 90% by weight of any butene present in the second recycle stream is converted to butane within the recycle hydrogenation unit.

16. The method of claim 1, further comprising drying the second recycle stream before or after passing to the recycle hydrogenation unit.

17. The method of claim 1, further comprising withdrawing a secondary hydrocarbon stream from the hydrocracking unit and passing the secondary hydrocarbon stream through a total hydrogenation unit to produce a total hydrogenated stream, the total hydrogenation unit converting olefins present in the secondary hydrocarbon stream to alkanes; and
feeding the total hydrogenated stream to the deisobutanizer unit.

18. A method of producing a fuel additive, comprising:
passing a first feed stream comprising C4 hydrocarbons through a fluid catalytic cracking unit forming a second feed stream;
passing the second feed stream through a hydrogenation unit forming a first process stream;
passing the first process stream through a methyl tertiary butyl ether synthesis unit producing a first recycle stream, wherein methanol and isobutylene are present in the methyl tertiary butyl ether synthesis unit in a molar ratio of one mole of isobutylene to 0.1 mole to 2 moles of methanol;
withdrawing a methyl tertiary butyl ether product from the methyl tertiary butyl ether synthesis unit;
withdrawing the first recycle stream from the methyl tertiary butyl ether synthesis unit and passing the first recycle stream through a hydration unit producing the fuel additive and a second recycle stream, wherein a temperature within the hydration unit is 30° C. to 200° C., a pressure within the hydration unit is 500 kiloPascals to 10,000 kiloPascals, and wherein greater than or equal to 90% by weight of any butene present in the first recycle stream is converted to butanol within the hydration unit;
withdrawing the fuel additive from the hydration unit, wherein the fuel additive comprises at least one of 2-butanol, tert-butyl alcohol, or C4 dimer;
passing the second recycle stream through a recycle hydrogenation unit, wherein at least a portion of butene present in the second recycle stream is converted to butane within the recycle hydrogenation unit;
passing the second recycle stream from the recycle hydrogenation unit and through a deisobutanizer unit forming an isobutylene-containing recycle stream; and
recycling the isobutylene-containing recycle stream from the deisobutanizer unit to the methyl tertiary butyl ether synthesis unit;
wherein greater than or equal to 40% by weight of any butane present in the second recycle stream is converted to isobutylene in the deisobutanizer unit prior to recycling to the methyl tertiary butyl ether synthesis unit;
wherein an octane number of the fuel additive is greater than or equal to 83 in accordance with the Anti-Knock Index; and
wherein a Reid vapor pressure of the fuel additive is 8 kiloPascals to 53 kilopascals.

19. The method of claim 18, wherein the deisobutanizer unit comprises a deisobutanizer column, an isomerization unit, and a dehydrogenation unit in series; and wherein the deisobutanizer column is operated at a temperature of 50 to 120° C. and a pressure of 800 to 100 kilopascals.

20. The method of claim 1, wherein methanol and isobutylene are present in the methyl tertiary butyl ether synthesis unit in a molar ratio of one mole of isobutylene to 1.06 moles to 1.2 moles of methanol.

* * * * *